United States Patent [19]

Ukihashi et al.

[11] 4,138,417

[45] Feb. 6, 1979

[54] PROCESS FOR PRODUCING PERFLUOROCARBOXYLIC ACID

[75] Inventors: Hiroshi Ukihashi, Tokyo; Takao Hayashi; Yukio Takasaki, both of Yokohama, all of Japan

[73] Assignee: Asahi Glass Company, Ltd., Tokyo, Japan

[21] Appl. No.: 793,303

[22] Filed: May 3, 1977

Related U.S. Application Data

[63] Continuation of Ser. No. 641,640, Dec. 17, 1975, abandoned.

[51] Int. Cl.$^2$ .......................... C09F 7/02; C11C 3/00
[52] U.S. Cl. .................................. 260/406; 260/408; 562/523; 562/533
[58] Field of Search .................. 260/406, 408, 530 R, 260/539 R

[56] References Cited

U.S. PATENT DOCUMENTS

| | | | |
|---|---|---|---|
| 2,819,279 | 1/1958 | Brown et al. | 260/413 |
| 2,996,525 | 8/1961 | Barnhart | 260/408 |
| 3,383,398 | 5/1968 | Peck et al. | 260/413 |
| 3,676,489 | 7/1972 | Ellis et al. | 260/533 R |
| 3,691,233 | 8/1972 | Ellis et al. | 260/533 R |

*Primary Examiner*—John Niebling
*Attorney, Agent, or Firm*—Oblon, Fisher, Spivak, McClelland & Maier

[57] ABSTRACT

A process for producing a perfluorocarboxylic acid comprises reacting a perfluoroalkyl olefin with ozone to produce a perfluoroalkyl ozonide and a perfluoroalkyl aldehyde and converting said perfluoroalkyl ozonide and perfluoroalkyl aldehyde to perfluorocarboxylic acid with an oxidizing agent.

7 Claims, No Drawings

PROCESS FOR PRODUCING PERFLUOROCARBOXYLIC ACID

This is a continuation, of application Ser. No. 641,640, filed Dec. 17, 1975 now abandoned.

BACKGROUND OF THE INVENTION

1. Field of the Invention

The present invention relates to a process for preparing perfluorocarboxylic acid. In particular, it relates to a novel process for producing perfluorocarboxylic acid in two steps.

2. Description of the Prior Art

It is known that perfluorocarboxylic acids are strong acids having excellent heat and chemical resistance. Various uses of perfluorocarboxylic acids have been proposed because of the special surface activity of perfluoroalkyl groups. For example, ammonium salts and alkali metal salts of perfluorocarboxylic acids are indispensable emulsifiers for the polymerization of fluorinated olefins such as tetrafluoroethylene and the like. Perfluorocarboxylic acids are also used as vaporization suppressants for volatile combustible organic liquids. Perfluorocarboxylic acids are also useful as intermediates for the preparation of fluorocarbon surfactants having excellent surface activities. Certain metal salts and polymers derived from perfluorocarboxylic acids are also useful as water-repelling and oil-repelling agents.

There are several synthetic methods for preparing perfluorocarboxylic acids. Among them, is the well-known Simons electrolytic fluorination process which provides a simple means of obtaining the acid.

$$RCOCl \xrightarrow{\text{anhydrous HF}} R_fCOF \xrightarrow{H_2O} R_fCOOH$$

However, the yield of the acid is very low because of the formation of cyclic ethers as well as of the cleavage of the carbon-carbon linkage.

Sulfur trioxide or chlorosulfonic acid can convert perfluoroalkyl iodide to the carboxylic acid.

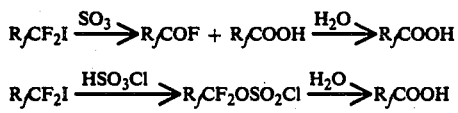

$$R_fCF_2I \xrightarrow{SO_3} R_fCOF + R_fCOOH \xrightarrow{H_2O} R_fCOOH$$

$$R_fCF_2I \xrightarrow{HSO_3Cl} R_fCF_2OSO_2Cl \xrightarrow{H_2O} R_fCOOH$$

The handling of the highly corrosive reagents at high temperatures (160-200° C.) is disadvantageous in large scale production.

The oxidation of perfluoroalkyl ethylene by potassium permanganate gives perfluorocarboxylic acid in fairly high yields.

$$R_fCH{=}CH_2 \xrightarrow{KMnO_4} R_fCOOK \xrightarrow{H+} R_fCOOH$$

In this process manganese dioxide is also formed, in an amount equivalent to the acid formed. In this process it is difficult to specify the product and it is necessary to recover the manganese dioxide.

Accordingly, there is a need for a simple direct process for preparing perfluorocarboxylic acids.

SUMMARY OF THE INVENTION

It is an object of the present invention to provide a process for producing perfluorocarboxylic acids having high purity in high yield.

It is another object of the present invention to provide a process for producing perfluorocarboxylic acids without using any highly corrosive reagents.

It is still another object of the present invention to provide a process for producing perfluorocarboxylic acids in which the product can be easily separated and purified.

It is a further object of this invention to provide a process for producing perfluorocarboxylic acids without the formation of solid by-products which are difficult to separate.

A still further object of this invention is to provide a novel clean process for producing perfluorocarboxylic acids which is especially effective for large scale production of such acids.

These and other objects of the present invention as will hereinafter become clear have been attained by a process for producing a perfluorocarboxylic acid which comprises a first step of reacting perfluoroalkyl olefins with ozone to produce a perfluoroalkyl ozonide and a perfluoroalkyl aldehyde and a second step of converting said perfluoroalkyl ozonide and perfluoroalkyl aldehyde to perfluorocarboxylic acid with an oxidizing agent.

DETAILED DESCRIPTION OF THE PREFERRED EMBODIMENTS

In the first step, perfluoroalkyl olefins having the formula $R_fCH = CR^1R^2$ easily react with ozone to form the perfluoroalkyl ozonide

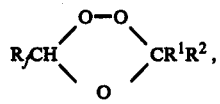

$$R_fCH\underset{\underset{O}{\diagdown}}{\overset{\overset{O-O}{\diagup}}{\diagup}}CR^1R^2,$$

perfluoroalkyl aldehyde $R_fCHO$, and optionally a minor amount of perfluorocarboxylic acid. $R_f$ represents a perfluoroalkyl group having 4 – 18 carbon atoms and $R^1$ and $R^2$ represent a hydrogen atom or a lower alkyl group. In the second step, the perfluoroalkyl ozonide as well as the perfluoroalkyl aldehyde are converted to perfluorocarboxylic acids with oxidizing agents.

In this invention, the perfluoroalkyl olefin starting materials have the formula

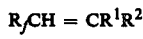

$$R_fCH = CR^1R^2$$

wherein $R_f$ represents a perfluoroalkyl group of 4 – 18 carbon atoms and $R^1$ and $R^2$ represent a hydrogen atom or a lower alkyl group, $R_1$ and $R_2$ are not critical and can be different. It is preferred to use as the starting material perfluoroalkyl ethylene which has the formula

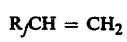

$$R_fCH = CH_2$$

Usually, perfluoroalkyl olefins are produced by an addition reaction of $R_fX$ with an olefin to form the compound $R_fCH_2CR^1R^2X$ which is then dehydrohalogenated, wherein X is preferably Br or I but can also be cl. The addition reaction of $R_fX$ with an olefin may be conducted in the presence of a free-radical catalyst with heating or with ultraviolet or radioactive irradiation. The production of $R_fCH_2CH_2X$ is disclosed in Haszeldine et al. J. Chem. Soc. 2856 (1949); ibid 3041 (1950); Part et al. J. Org. Chem., 23, 1166 (1958); and USP 3,145,222 (1964).

The perfluoroalkyl ethylhalide $R_fCH_2CH_2X$ may be converted to perfluoroalkyl ethylene, $R_fCH = CH_2$, by dehydrohalogenation. It is also possible to use perfluoroalkyl ethylene formed as a by-product in certain reactions using $R_fCH_2CH_2X$ as a starting material (Japanese Patent Publication No. 18112/1954 and Japanese Unexamined Patent Publication No. 103504/1973). In the formula, $R_f$ represents a perfluoroalkyl group having 4 – 18 carbon atoms, preferably 6 – 15 carbon atoms and $R^1$ and $R^2$ represent a hydrogen atom or a $C_{1-5}$ lower alkyl group.

The reaction of perfluoroalkyl olefins with ozone in the first step can be conducted at 0°–120° C. preferably 10° – 100° C. When the reaction temperature is too high, the yield is low and the necessary apparatus and operation are disadvantageous. On the other hand, when the reaction temperature is too low, the viscosity of the reaction system is high and the reaction rate is low. The ozone source can be pure ozone but is usually an ozone containing gas such as oxygen or air. For example, ozone or ozone containing oxygen diluted with an inert gas such as nitrogen gas may be used. The ozone content of the gas is usually in the range of 0.1 – 100 vol.%, preferably 1 – 10 vol.% and especially 2 – 5 vol.%. The first step of the reaction is preferably conducted in an organic solvent which is inert to ozone, such as carbon tetrachloride, tetrachlorodifluoroethane, formic acid, acetic acid and the like. The molar ratio of ozone to $R_fCH = CR^1R^2$ in the reaction is preferably greater than 1 and is preferably 1 – 3, especially 1.2 – 1.5. The reaction time is not critical and is usually 0.1 – 10 hr., preferably 1 – 10 hr. and especially 3 – 5 hr.

The conversion of $R_fCH = CR^1R^2$ may be 100%. When the conversion of $R_fCH = RC^1R^2$ is low, the formation of perfluorocarboxylic acid does not occur in the first step where said ozonide and aldehyde are formed. However, when the conversion of $R_fCH=CR^1R^2$ is high, a minor amount of perfluorocarboxylic acid is produced by the oxidation of said aldehyde. For example, when $R_fCH—CR^1R^2$ is completely converted, about 10% of perfluorocarboxylic acid is produced. The amount of said ozonide formed is about 60 – 65% of the product and the amount of said aldehyde is about 20 – 35% of the product in such a case. The perfluorocarboxylic acids which are produced in the first step are the object products of the present invention and, accordingly, it is possible to feed the mixture of perfluorocarboxylic acid, ozonide and aldehyde directly to the second step. It is also possible to separate the perfluorocarboxylic acid from the reaction mixture of the first step and then to feed the ozonide and aldehyde to the second step. In an industrial operation, the former method is advantageous.

In the second step, perfluoroalkyl ozonide as well as perfluoroalkyl aldehyde can be converted to perfluorocarboxylic acid with oxidizing agents. Various oxidizing agents can be used. Suitable oxidizing agents include hydrogen peroxide, organic peroxides, oxygen, ozone, ozone-oxygen mixtures, ozone-formic acid mixtures, peracetic acid, performic acid, perbenzoic acid and the like. It is possible to accelerate the reaction by using a metal ion such as cobalt ion with the oxidizing agent. When ozone is used as an oxidizing agent in the second step, it is possible to conduct the reaction by feeding ozone in the reaction mixture produced in the first step without separating said ozonide and said aldehyde after the reaction of $R_fCH = CR^1R^2$ with ozone. Usually, ozone is fed into the reaction mixture at the higher reaction temperature suitable for the second step. In this case, it is preferred to use the ozone-containing oxygen or air of the first step. It is also possible to continuously feed the ozone-containing oxygen or air from the first step to the second step.

In the second step of this invention, it is preferred to use a liquid oxidizing agent such as hydrogen peroxide, peracids and the like, especially peracids such as peracetic acid, performic acid, perbenzoic acid and the like. Perfluoroalkyl ozonide and perfluoroalkyl aldehyde can be substantially converted to perfluorocarboxylic acid by an oxidizing decomposition using hydrogen peroxide. Perfluoroalkyl ozonide and perfluoroalkyl aldehyde can be converted to perfluorocarboxylic acid with a selectivity of 100% by oxidative decomposition using such a peracid. Hydrogen peroxide is usually used as an aqueous solution of a concentration of 5 – 60%, preferably 20 – 40%. When a peracid is used in the second step, it is preferred to form it in the reaction system. For example, an organic acid such as benzoic acid, or the like, or a liquid carboxylic acid such as acetic acid, formic acid propionic acid or the like, can be used together with hydrogen peroxide for the conversion of said ozonide and said aldehyde and a peracid is formed by the reaction of said organic acid and hydrogen peroxide. The peracid acts as an oxidizing agent. Using this method, the ozonide and aldehyde can be converted to perfluorocarboxylic acid with a conversion of 100% and a selectivity of 100%. The oxidizing decomposition by the peracid can be conducted at a relatively low temperature because of the high reaction rate. Accordingly, from these viewpoints, it presents the optimum embodiment of this invention.

In the conversion of the ozonide and aldehyde to perfluorocarboxylic acid in the second step, the molar ration of the oxidizing agent to the ozonide and the aldehyde and the reaction temperature and similar parameters can be conventionally selected depending upon the type of the oxidizing agent employed. For example, perfluorocarboxylic acid can be produced by reacting 1.2 – 10 moles, especially 2 – 5 moles, of hydrogen peroxide with 1 mole of the total amount of the ozonide and aldehyde at 40-150° C., preferably 70–100° C., for 3–20 hours. Perfluorocarboxylic acid can also be produced by feeding 1 – 10 moles, especially 2 – 5 moles of ozone per 1 mole of the total amount of the ozonide and aldehyde at 40-150° C., preferably 70–100° C. for 2-15 hours, preferably 3-6 hours. When hydrogen peroxide is combined with an organic acid or a peracid is used as the oxidizing agent for the second step, it is possible to conduct the reaction at a relatively low temperature such as 0–100° C., especially 30–70° C. In this case, it is preferred to use 1 – 10 moles, especially 2 – 5 moles of said peracid to 1 mole of the total amount of the ozonide and aldehyde. An organic acid can be used as a solvent. Accordingly, an excess of the organic acid related to hydrogen peroxide can be used. The oxidative decomposition reaction using the peracid can be conducted for a relatively short time, such as 0.5 – 4, especially 1 – 3 hours. In general, the molar ratio of the oxidizing agent to the total amount of the ozonide and aldehyde in the second step is preferably more than 1, such as 1 – 10, especially 2 – 5. The reaction temperature is usually 0–150° C., especially 30–100° C. It is possible to conduct the reaction of the second step in an organic solvent such as carbon tetrachloride, tetrachlorodifluoroethane, formic acid, acetic acid and the like or in an aqueous medium.

The resulting perfluorocarboxylic acid can be easily separated and purified from the by-products, e.g., formic acid, acetic acid and the solvent, and the like by conventional methods. For example, when carbon tetrachloride is used as the solvent, ozone is used as the oxidizing agent and the reaction mixture is cooled to below 0° C. Perfluorocarboxylic acid, having a low solubility, is precipitated. It can be separated from the carbon tetrachloride solution containing formic acid by filtration. When an aqueous hydrogen peroxide solution is used as the oxidizing agent and the reaction mixture is allowed to stand at 70–80° C., an upper phase of hydrogen peroxide, formic acid and water is separated from a lower phase of perfluorocarboxylic acid and carbon tetrachloride. Accordingly, the lower phase can be removed and then perfluorocarboxylic acid can be separated from carbon tetrachloride by the aforementioned cooling and filtering method. When a combination of aqueous hydrogen peroxide solution and acetic acid is used as the oxidizing agent in the second step, water and acetic acid are separated from perfluorocarboxylic acid by azeotropic distillation using excess toluene. The toluene solution is cooled to below 10° C., and the precipitated perfluorocarboxylic acid can be separated from toluene by filtration.

The invention will be further illustrated by certain examples which are included for purposes of illustration only and are not intended to be limiting.

EXAMPLE 1 (Production of ozonide and aldehyde)

In a 500 ml four necked flask equipped with a stirrer, a reflux condenser, a gas inlet and a thermometer, 400 g of $C_8F_{17}CH=CH_2$ was charged. The contents were heated to 50° C. and ozone-containing oxygen (ozone concentration of 0.2 g/l) was fed at a rate of 70 liter/hr. for 3.5 hours with stirring. After the reaction, according to a gas chromatographic analysis of the reaction mixture, the conversion of $C_8F_{17}CH = CH_2$ was 100% and the reaction mixture included 65% of ozonide,

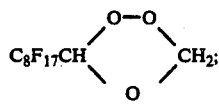

25% of aldehyde $C_8F_{17}CHO$;
8% of perfluorocarboxylic acid, $C_8F_{17}COOH$; and
2% of formic acid.

EXAMPLE 2 (Conversion of ozonide and aldehyde)

In a 500 ml four necked flask equipped with a stirrer, a reflux condenser, a dropping funnel and a thermometer, 200 g of the reaction mixture of Example 1 including 65% of said ozonide, 25% of said aldehyde, 8% of said perfluorocarboxylic acid and 2% of formic acid, and 20 g of a 30% aqueous solution of hydrogen peroxide were charged. The mixture was heated to 90° C. while slowly stirring. After 1 hour, 40 g of a 30% aqueous solution of hydrogen peroxide was added dropwise during 2 hours. The temperature was kept at 90° C., and the reaction was continued for 1 hour with stirring. At this time, the conversions of the ozonide and the aldehyde reached about 100%. Accordingly, 500 g of perchloroethylene was added and the mixture was vigorously stirred at 70° C., and was allowed to stand for 1 hour. The lower organic phase was separated. The upper aqeuous phase was admixed with 500 g of perchloroethylene and the same operation was repeated. The lower organic phase was separated. The organic phase obtained by the same operation was admixed with the two organic phases and the mixture was cooled to 0° C. The precipitated white solid was filtered and was dried in a vacuum drier, to obtain a mixture consisting of 92% of $C_8F_{17}COOH$, and 8% of $C_7F_{15}COOH$. (Yield 95%).

EXAMPLE 3 (Conversion of ozonide and aldehyde)

In the flask of Example 2, 150 g of the reaction mixture of Example 1, and 40 g of a 30% aqueous solution of hydrogen peroxide and 100 g of acetic acid were charged. The reaction of the mixture was conducted at 50° C. for 2 hours. At this time, the conversions of the ozonide and aldehyde were 100%. After the reaction, 560 g of toluene was added to the reaction mixture and a mixture of toluene-water-acetic acid was removed by distillation by azeotropic distillation. A white solid, precipitated in the excess of the toluene, was filtered and dried in vacuum at 20° C. to obtain 140 g of $C_8F_{17}COOH$ having a purity of 99.5%. (Yield 99%). No $C_7F_{15}COOH$ was detected.

EXAMPLE 4 (Conversion of ozonide and aldehyde)

The process of Example 3 was repeated except for using 43 g of peracetic acid instead of the aqueous hydrogen peroxide solution. As a result, 138 g of $C_8F_{17}COOH$ having a purity of 98.7% was obtained.

EXAMPLE 5 (Conversion of ozonide and aldehyde)

The reaction mixture of Example 1 was oxidized by using $O_2$. In a 200 ml four necked flask equipped with a stirrer, a reflux condenser, a gas inlet and a thermometer, 200 g of a mixture of 65% of

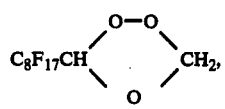

25% of $C_8F_{17}CHO$, 8% of $C_8F_{17}COOH$, and 2% of other material, were charged and the contents were heated to 90° C. Oxygen was introduced at a rate of 20 liter/hr. The temperature of the contents was maintained at 90° C. and oxygen was continuously fed for 10 hours. According to a gas chromatographic analysis of the reaction product, the conversion of

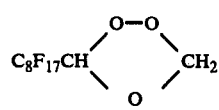

was 100%. The reaction product was dissolved in 2 kg of carbon tetrachloride at 65° C. It was then recrystallized by cooling the solution to 0° C. The precipitated white crystals were filtered and dried in a vacuum drier oven to obtain 160 g of a mixture of 89% of $C_8F_{17}COOH$ and 11% of $C_7F_{15}COOH$.

EXAMPLE 6 (Conversion of ozonide and aldehyde)

The reaction mixture was obtained using $O_2$ + $(C_8F_{17}COO)_3CO$. The process of Example 5 was repeated except for using 1 g of $(C_8F_{17}COO)_3CO$ as catalyst and reacting for 3 hours. As a result, 130 g of a mixture of 74% of $C_8F_{17}COOH$ and 26% of $C_7F_{15}COOH$ was obtained.

EXAMPLE 7

In a 300 ml four necked flask equipped with a stirrer, a reflux condenser, a gas inlet and a thermometer, 300 g of $C_8F_{17}CH = CH_2$ was charged and was heated to 80° C. The contents were vigorously stirred and ozone-containing air (0.34g/liter of ozone) was fed at a rate of 80 liter/hr. The temperature of the reaction mixture rose to 93° C. after 30 minutes, and the ozone-containing air was continuously fed for 1 hour. At this time, the conversion of $C_8F_{17}CH = CH_2$ was 100%. A reaction mixture including 58% of said ozonide, 17% of said aldehyde and 22% of perfluorocarboxylic acid was obtained. The reaction mixture was heated to 100° C. and the ozone-containing air was fed for 1.5 hours at the same flow-rate. The resulting reaction mixture was dissolved in 1.5 kg of toluene at 100° C. A small amount of insoluble matter was filtered, and the toluene solution was cooled at 0° C. to precipitate a white solid. The white solid was dried in a vacuum drier oven after filtering. As a result, 298 g of a mixture consisting of 86% of $C_8F_{17}COOH$ and 14% of $C_7F_{15}COOH$ was obtained.

EXAMPLE 8 (Production of ozonide and aldehyde)

In the flask of Example 7, 100 g of $C_6F_{13}CH = CHCH_3$ and 200 g of carbon tetrachloride were charged and the mixture was maintained at 20° C. Ozone-containing air (0.05 g/liter of ozone) was fed at a rate of 100 liter/hr. for 4 hours with vigorous stirring during the reaction. According to a gas chromatographic analysis, the conversion of $C_6F_{13}CH = CHCH_3$ was 100% and the reaction mixture included

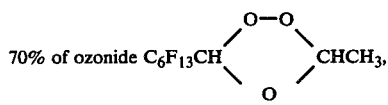

70% of ozonide $C_6F_{13}CH \diagdown O \diagup CHCH_3$,

20% of aldehyde $C_6F_{13}CHO$, 6% of perfluorocarboxylic acid $C_6F_{13}COOH$ and 4% of other components, e.g., acetic acid.

EXAMPLE 9 (Conversion of ozonide and aldehyde)

In the flask of Example 7, 100 g of the reaction mixture of Example 8, 5 g of 80% formic acid and 200 g of chloroform were charged. Ozone-containing oxygen (0.1 g/liter of ozone) was fed at a rate of 56 liter/hr. to the reaction mixture with vigorous stirring. After 5 hours, the feed of the gas was stopped. Chloroform, formic acid and acetic acid were removed by distillation in a vacuum to obtain 97 g of a product: 91 % of $C_6F_{13}COOH$ and 9 % of $C_5F_{11}COOH$ as white solid.

EXAMPLE 10

In the reactor of Example 1, 400 g of $C_{10}F_{21}CH=CH_2$ and 200 g of acetic acid were charged and oxygen containing 0.1 g/liter of ozone was introduced at a rate of 30 liter/hr. The temperature of the contents was maintained at 20° C. and the ozone-containing oxygen was fed for 12 hours with stirring. According to a gas chromatographic analysis of the reaction product, the conversion of $C_{10}F_{21}CH = CH_2$ was 100% and the reaction mixture was an acetic acid solution containing

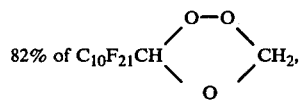

82% of $C_{10}F_{21}CH \diagdown O \diagup CH_2$,

14% of $C_{10}F_{21}CHO$, 3% of $C_{10}F_{21}COOH$ and 1% of formic acid.

EXAMPLE 11

In the reactor of Example 2, 400 g of the acetic acid solution produced in Example 10 was charged. The solution contained 236 g of

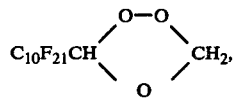

$C_{10}F_{21}CH \diagdown O \diagup CH_2$, 40 g of $C_{10}F_{21}CHO$ 9 g of $C_{10}F_{21}COOH$ and 3 g of formic acid. The contents were heated to 60° C. and 350 g of 30% acetic acid solution of perbenzoic acid was added dropwise from a dropping funnel at a rate of 100 g/hr. After the addition, the mixture was stirred at 60° C. for 1 hour. The conversions of the ozonide and the aldehyde reached 100%. Then, the refluxing condensor was removed and a Vigreau distillation column having a length of 30 cm was attached. The contents were heated to distill 350 g of acetic acid. The remainder was poured into 1 kg of toluene. The precipitate was filtered and dried in a vacuum drier oven to obtain 262 g of $C_{10}F_{21}COOH$ (purity of 98.5%).

Having now fully described the invention, it will be apparent to one or ordinary skill in the art that many changes and modifications can be made thereto without departing from the spirit or scope of the invention as set forth herein.

What is claimed as new and desired to be secured by letters patent of the United States is:

1. A process of producing a perfluorocarboxylic acid, which comprises:
    reacting a perfluoroalkyl olefin with an ozone containing gas having an ozone content of 1 – 10 volume percent to produce a perfluoroalkyl ozonide and perfluoroalkyl aldehyde and converting said perfluoroalkyl ozonide and perfluoroalkyl aldehyde to perfluorocarboxylic acid with an oxidizing agent.

2. The process for producing perfluorocarboxylic acid in claim 1, wherein ozone-containing oxygen or air is used as the ozone source in the first step.

3. The process of producing perfluorocarboxylic acid in claim 1, wherein an organic solvent selected from the group consisting of carbon tetrachloride, tetrachlorodifluoroethane, formic acid and acetic acid which is inert to ozone, is added in the first step.

4. The process for producing perfluorocarboxylic acid of claim 1, wherein hydrogen peroxide or a peracid is used as the oxidizing agent in the second step.

5. A process for producing perfluorocarboxylic acid in claim 1, wherein ozone or an ozone containing gas selected from the group consisting of an ozone-oxygen mixture, air containing ozone and ozone in an inert gas is used as the oxidizing agent in the second step.

6. The process for producing perfluorocarboxylic acid of claim 1, wherein a liquid carboxylic acid selected from the group consisting of formic acid, acetic acid and propionic acid is used as a solvent in the second step.

7. The process for producing perfluorocarboxylic acid of claim 1, wherein the molar ratio of ozone to perfluoroalkyl olefin in the first step is 1 – 3 molar ratio of the oxidizing agent to the total of the ozonide and the aldehyde in the second step is 1 –10.

* * * * *